United States Patent
Lee et al.

(10) Patent No.: US 12,162,999 B2
(45) Date of Patent: *Dec. 10, 2024

(54) DODECYL SULFATE-DOPED POLY(3,4-ETHYLENEDIOXYTHIOPHENE) FILM AND MANUFACTURING METHOD THEREFOR

(71) Applicant: FLEXOLUTION, Yongin-si (KR)

(72) Inventors: Jung Won Lee, Seoul (KR); Sung Soo Kim, Daejeon (KR); Feng Ma, Daejeon (KR)

(73) Assignee: FLEXOLUTION, Yongin-si (KR)

( * ) Notice: Subject to any disclaimer, the term of this patent is extended or adjusted under 35 U.S.C. 154(b) by 648 days.

This patent is subject to a terminal disclaimer.

(21) Appl. No.: 17/284,069

(22) PCT Filed: Aug. 20, 2019

(86) PCT No.: PCT/KR2019/010583
§ 371 (c)(1),
(2) Date: Apr. 9, 2021

(87) PCT Pub. No.: WO2020/075967
PCT Pub. Date: Apr. 16, 2020

(65) Prior Publication Data
US 2021/0317277 A1    Oct. 14, 2021

(30) Foreign Application Priority Data
Oct. 10, 2018   (KR) .................... 10-2018-0120286

(51) Int. Cl.
| | | |
|---|---|---|
| *C08J 5/18* | (2006.01) | |
| *B05D 1/00* | (2006.01) | |
| *B05D 3/00* | (2006.01) | |
| *C07C 303/44* | (2006.01) | |
| *C08K 5/41* | (2006.01) | |
| *H01B 1/12* | (2006.01) | |

(52) U.S. Cl.
CPC ........ *C08J 5/18* (2013.01); *B05D 1/60* (2013.01); *B05D 3/007* (2013.01); *C07C 303/44* (2013.01); *C08K 5/41* (2013.01); *H01B 1/127* (2013.01); *C07B 2200/13* (2013.01); *C08J 2381/00* (2013.01)

(58) Field of Classification Search
CPC .......... C08J 5/18; C08J 2381/00; B05D 1/60; B05D 3/007; C07C 303/44; C08K 5/41; H01B 1/127; C07B 2200/13
See application file for complete search history.

(56) References Cited

U.S. PATENT DOCUMENTS

2015/0114460 A1*  4/2015  Ting .................... B01J 31/10
                                                     502/1
2018/0046035 A1*  2/2018  Lan ................. G02F 1/133784

FOREIGN PATENT DOCUMENTS

| KR | 1020140067237 | 6/2014 | |
|---|---|---|---|
| WO | 2008-130326 | 10/2008 | |
| WO | 2009-054814 | 4/2009 | |
| WO | 2014-201471 | 12/2014 | |
| WO | WO-2014201471 A1 * | 12/2014 | ............. H01B 1/127 |

OTHER PUBLICATIONS

Han, M.G. and Foulger, S. (2006), Facile Synthesis of Poly(3,4-ethylenedioxythiophene) Nanofibers from an Aqueous Surfactant Solution. Small, 2: 1164-1169. https://doi.org/10.1002/smll.200600135 (Year: 2006).*
IUMRS-ICEM 2018 held Aug. 19-24, Daejeon, Korea, Presentation Material "A Glass Capillary-Written and then Vapor Phase-Polymerized PEDOT Conductor with Stability in Water", presented by Feng Ma and Sungsoo Kim.
PCT International Search Report (ISR).
"Fe(DS)3, an efficient Lewis acid-surfactant-combined catalyst (SASC) for the one pot synthesis of chromenor[4,3-b] chromene derivatives by assembling the basi building blocks," Pradhan et. al., Tetrahedron Letters 54 (2013) 3105-3110.
"Improvement of the Electrosynthesis and Physicochemical Properties of Poly(3,4-ethylenedioxythiophene) Using a Sodium Dodecyl Sulfate Micellar Aqueous Medium," Sakmeche et. al., Langmuir 1999, 15, 2566-2574.
"Imidazolium Iodide-Doped PEDOT Nanofibers as Conductive Catalysts for Highly Efficient Solid-State Dye-Sensitized Solar Cells Employing Polymer Electrolyte," Kim et. al., ACS Appl. Mater. Interface 2018, 10, 2537-2545.
Improvement of the electrosynthesis and physiochemical properties of poly(3, 4-ethylendioxythiophene) using a sodium dodecyl sulfate micellar aqueos medium, American chemical society, 1999, vol. 15, No. 7, pp. 2566-2574.
Office Action from Japan Patent Office on May 10, 2022.

(Continued)

*Primary Examiner* — Callie E Shosho
*Assistant Examiner* — Bethany M Miller

(57) ABSTRACT

Proposed are a dodecyl sulfate-doped PEDOT film and a manufacturing method therefor, the method including: coating, on a substrate, an oxidizing agent film including a dodecyl sulfate metal salt such as Fe(DS)₃; and forming a PEDOT film by vapor phase polymerization. The dodecyl sulfate-doped PEDOT film according to the present disclosure has excellent electrical conductivity so as to be capable of replacing a metal, and has excellent mechanical durability, light transmittance, and aqueous solution stability.

13 Claims, 15 Drawing Sheets

(56) References Cited

OTHER PUBLICATIONS

Polymeric Material with Metal-Like Conductivity for Next Generation Organic Electronic Devices; Manrico V. Fabretto, et. al., Chemistry of Materials. 2012.
Single-Crystal Poly(3,4-ethylenedioxythiophene) Nanowires with Ultrahigh Conductivity; Boram Cho, et. al., American Chemical Society, 2014.
Structure and Dopant Engineering in PEDOT Thin Films: Practical Tools for a Dramatic Conductivity Enhancement; Magatte Gueye, et. al., Chemistry of Materials. 2016.
High electrical conductivity and carrier mobility in oCVD PEDOT thin films by engineered crystallization and acid treatment; Xiaoxue Wang, et. al., Science Advances. 2018.
Supplementary Information: Self-inhibited Polymerization of Micrometer-thick PEDOT Films with High Electrical Conductivity: Roles of Anion; Wei Shi, et. al.
Micron-thick highly conductive PEDOT films synthesized via self-inhibited polymerization: roles of anions; Wei Shi, et. al., NPG Asia Materials. 2017.
Highly Conductive Poly(3,4-ethylenedioxythiophene):Poly(styrenesulfonate) Films Using 1-Ethyl-3-methylimidazolium Tetracyanoborate Ionic Liquid; Chantal Badre, et. al., Adv Funct Mater. 2012.
A highly stretchable, transparent, and conductive polymer; Yue Wang, et. al., Science Advances. 2017.
Large-scale Flexible and Highly Conductive Carbon Transparent Electrodes via Roll-to-roll Process and Its High Performance Lab-scale ITO-free PSCs; Xiotian Hu, et. al., Chem. Mater., 2014.
A Mechanically Robust Conducting Polymer Network Electrode for Efficient Flexible Perovskite Solar Cells; Xiaotian Hu, et. al., Elsevier. 2019.
Significant Vertical Phase Separation in Solvent-Vapor-Annealed Poly(3,4-ethylenedioxythiophene):Poly(styrene sulfonate) Composite Films Leading to Better Conductivity and Work Function for High-Performance Indium Tin Oxide-Free Optoelectronics; Jun-Seok Yeo, et. al., American Chemical Society. 2012.
Highly Conductive PEDOT:PSS Electrode with Optimized Solvent and Thermal Post-Treatment for ITO-Free Organic Solar Cells; Yang Hyun Kim, et. al., Adv Funct Mat. 2011.
Highly conductive poly(3,4-ethylenedioxythiophene):poly(styrene sulfonate) films treated with an amphiphilic fluoro compound as the transparent electrode of polymer solar cells; Yijie Xia, et. al., Energy Environ Sci, 2012.
Highly conductive PEDOT:PSS electrode by simple film treatment with methanol for ITO-free polymer solar cells; Desalegn Alemu, et. al., Energy Environ Sci. 2012.
Highly Conductive PEDOT:PSS Nanofibrils Induced by Solution-Processed Crystallization; Nara Kim, et. al., Advanced Materials, 2014.
PEDOT:PSS Films with Greatly Enhanced Conductivity via Nitric Acid Treatment at Room Temperature and Their Application as Pt/TCO-Free Counter Electrodes in Dye-Sensitized Solar Cells; Changbong Yeon, et. al., Adv Electron Mater. 2015.
Conductivity enhancement of PEDOT:PSS films via phosphoric acid treatment for flexible all-plastic solar cells; Wei Meng, et. al., Appl Mater Interfaces, 2015.
Bendable ITO-free Organic Solar Cells with Highly Conductive and Flexible PEDOT:PSS Electrodes on Plastic Substrates; Xi Fan, et. al., Appl Mater Interfaces, 2015.
Fully soluble self-doped poly(3,4-ethylenedioxythiophene) with an electrical conductivity greater than 1000 S cm$^{-1}$; Hirokazu Yano, et. al., Science Advances, 2019.

\* cited by examiner (oxidizing agent film coating) (PEDOT film vapor phase polymerization) (washing/drying)

FIG. 8
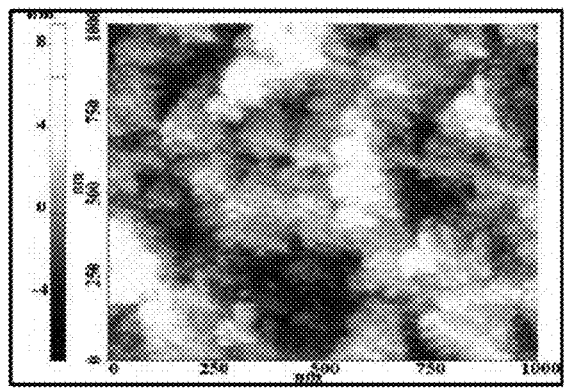
(a)
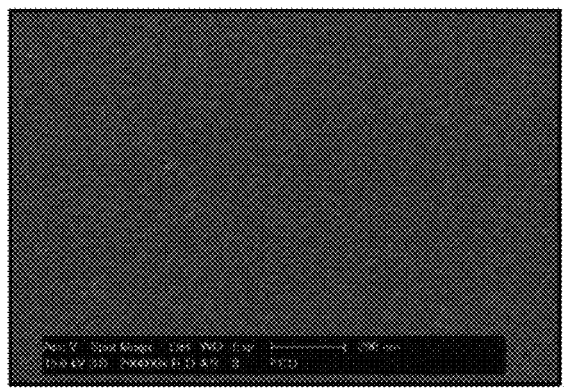
(b)
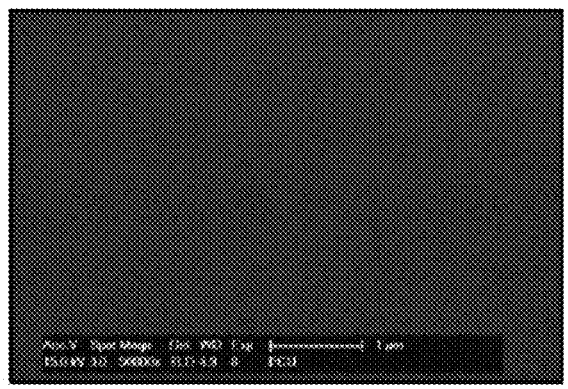
(c)
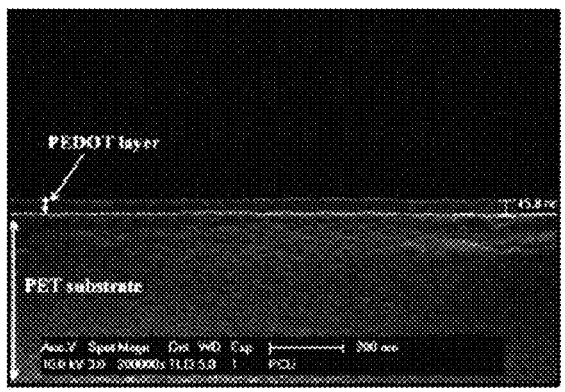
(d)
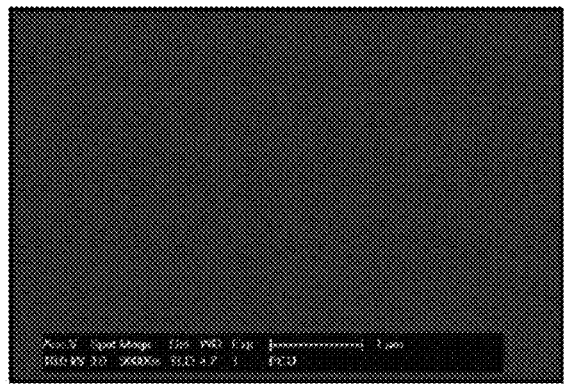
(e)
(f)

FIG. 14
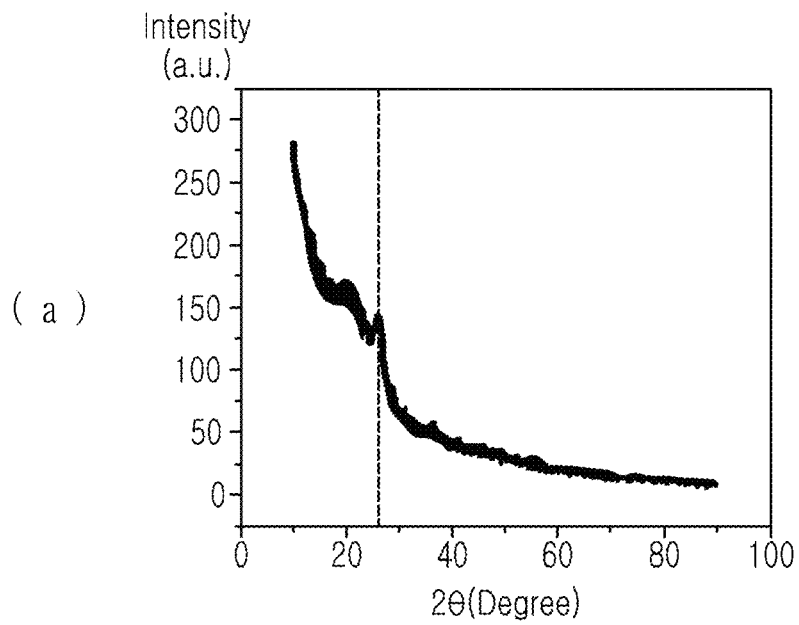
(a)
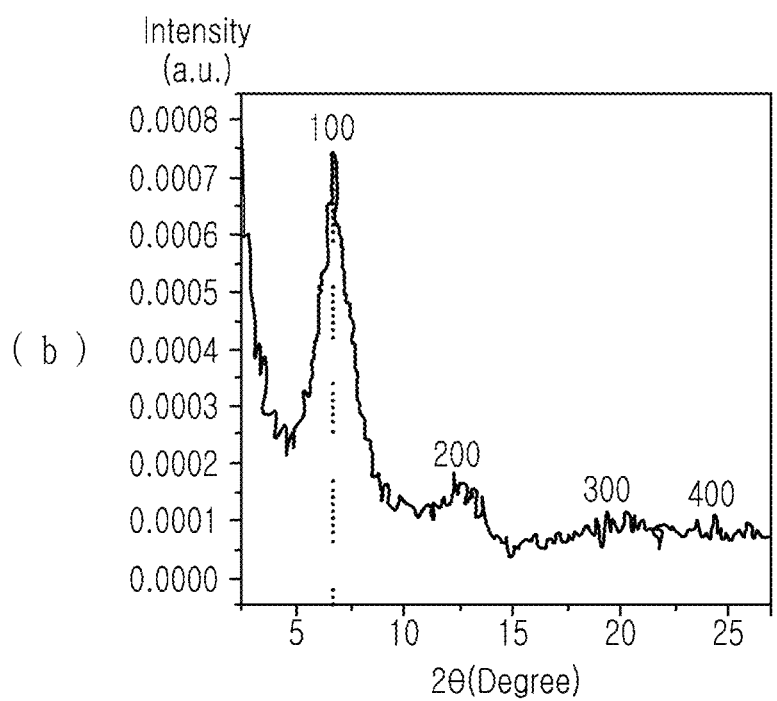
(b)

(a)　　　　　　　(b)　　　　　　　(c)

DODECYL SULFATE-DOPED POLY(3,4-ETHYLENEDIOXYTHIOPHENE) FILM AND MANUFACTURING METHOD THEREFOR

CROSS-REFERENCE TO RELATED APPLICATION

This application is a U.S. national phase application of PCT International Application PCT/KR2019/010583, filed Aug. 20, 2019, which claims priority to Korean Patent Application 10-2018-0120286, filed Oct. 10, 2018, the contents of which are incorporated herein by reference in their entirety.

TECHNICAL FIELD

The present disclosure relates generally to a PEDOT film having excellent properties and a manufacturing method therefor and, more particularly, to a PEDOT film doped with dodecyl sulfate and a manufacturing method therefor.

BACKGROUND ART

Due to their characteristics of flexibility, light weight, and low cost, organic conductive materials are in the spotlight as electrode materials for various electronic devices including flexible devices. In order to be used as an electrode material, an organic conductive material is required to have high electrical conductivity. However, among various conductive polymers, only a few have been actively studied, and poly(3,4-ethylenedioxythiophene) (hereinafter referred to as 'PEDOT') is a representative material.

Due to its small bandgap energy of about 1.5 to 1.7 eV, transparency, and excellent thermal stability and atmospheric stability, PEDOT is in the spotlight as a transparent flexible electrode of various devices such as organic transistors, photovoltaic devices, displays, and organic light-emitting diodes (OLEDs).

Examples of methods of forming PEDOT films include electropolymerization (EP), vapor phase polymerization (VP), and solution casting polymerization (SCP). Of these, electropolymerization has a limitation in that coating is possible only on a conductive surface, and solution casting polymerization not only requires advanced technology to obtain a homogeneous film, but also has a problem in that due to a short pot life of a polymerization mixture, insoluble PEDOT aggregates are formed in a solution after 10 to 20 minutes. On the other hand, vapor phase polymerization is a method in which EDOT, a monomer of PEDOT, is vaporized and polymerized on a substrate coated with an oxidizing agent, and has an advantage of relatively easily obtaining a high-purity homogeneous PEDOT film. In addition, it has been reported that the PEDOT film obtained by vapor phase polymerization generally exhibits superior electrical conductivity compared to the case of using other methods.

However, electrical conductivities of the PEDOT film reported so far are not sufficient to replace a metal electrode, and the further improvement of the electrical conductivity of the PEDOT film is regarded as an important task. In addition, in order to apply the PEDOT film to a flexible device, a display, a bio device, etc., mechanical durability, visible light transmittance, aqueous solution resistance, etc. have to be secured, and thus many improvements are required for these film properties.

Meanwhile, in the formation of the PEDOT film by vapor phase polymerization, the oxidizing agent not only plays a very important role as a polymerization initiator, but is also a key material in which an anion of the oxidizing agent acts as a dopant for a polymer. Examples of known oxidizing agents include $FeCl_3$, $H_2O_2$, $CuCl_2$, $HAuCl_4$, Fe(III) tosylate $(Fe(Tos)_3)$, iron (III) fluoromethanesulfonate $(Fe(OTf)_3)$, iron(III) fluride $(FeF_3)$, etc. However, these oxidizing agents are highly reactive and tend to be easily crystallized, making it difficult to efficiently polymerize PEDOT and control the reaction thereof, and generate defects in the film and thus are not suitable as oxidizing agents for forming a high-quality PEDOT film. In addition, the easily crystallized oxidizing agents prevent efficient doping of oxidizing agent anions when a polymer film is grown, so there is a limitation in synthesizing a polymer film having high electrical conductivity.

To lower high acidity of the oxidizing agents and control reactivity thereof, inhibitors such as diurethanediol (DUDO), poly(ethylene glycol)-block-poly(propylene glycol)-block-poly(ethylene glycol) (PEG-PPG-PEG), etc. are usually used. However, in this case, there is a problem in that the inhibitor remains in the PEDOT film, which adversely affects electrical conductivity and film stability. Therefore, there is a need for a new oxidizing agent capable of forming a highly stable PEDOT film by vapor phase polymerization without the use of additives such as inhibitors.

DISCLOSURE

Technical Problem

Accordingly, the present disclosure has been made keeping in mind the above problems occurring in the related art, and an objective of the present disclosure is to provide a PEDOT film having excellent electrical conductivity so as to be capable of replacing a metal electrode.

Another objective of the present disclosure is to provide a PEDOT film excellent in mechanical durability, flexibility, visible light transmittance, and aqueous solution resistance.

Still another objective of the present disclosure is to provide a method capable of forming a high-quality PEDOT film.

Yet another objective of the present disclosure is to provide a novel oxidizing agent suitable for forming a PEDOT film by vapor phase polymerization without requiring the addition of an inhibitor, and to provide a method for synthesizing the same.

Technical Solution

A PEDOT film according to an embodiment of the present disclosure may be a PEDOT film including dodecyl sulfate as a dopant. The PEDOT film may be formed by vapor phase polymerization using a dodecyl sulfate metal salt as an oxidizing agent, and dodecyl sulfate metal salt may be $Fe(DS)_3$. The PEDOT film may be formed as an electrode of an electronic device.

An amount of the dodecyl sulfate dopant may be within a range of 5 to 50 wt %. Here, the PEDOT film may have a lamella structure in which at least one, preferably two dodecyl sulfate molecules are doped between the PEDOT molecular layers.

Furthermore, the PEDOT film according to the embodiment of the present disclosure may have an electrical conductivity of equal to or greater than 5,500 S/cm, preferably equal to or greater than 10,000 S/cm.

Furthermore, the PEDOT film according to the embodiment of the present disclosure may have a light transmittance of equal to or greater than 90% at a thickness of 20 nm for a wavelength of 550 nm.

Furthermore, the PEDOT film according to the embodiment of the present disclosure may have a change in electrical resistance equal to or less than 9% after 300,000 bending cycles, or a change in electrical resistance of equal to or less than 10% after stretching in length by 30%.

Furthermore, the PEDOT film according to the embodiment of the present disclosure may have a change in electrical resistance of equal to or less than 5% even after immersion in deionized water for at least 20 days.

A method of manufacturing a PEDOT film according to an embodiment of the present disclosure may include: coating, on a substrate, an oxidizing agent film including a dodecyl sulfate metal salt; forming a PEDOT film on the substrate coated with the oxidizing agent film by vapor phase polymerization; and washing and drying the PEDOT film. The dodecyl sulfate metal salt may include $Fe(DS)_3$. Furthermore, the method may be free from use of an inhibitor.

A method of preparing an oxidizing agent for use in manufacturing a PEDOT film by vapor phase polymerization according to the present disclosure may include: precipitating a dodecyl sulfate metal salt by recrystallization; washing the precipitated dodecyl sulfate metal salt; and performing vacuum freeze drying. The dodecyl sulfate metal salt may include $Fe(DS)_3$.

Here, the precipitating of the dodecyl sulfate metal salt by recrystallization may further include removing impurities by centrifugation.

Furthermore, the precipitating of the dodecyl sulfate metal salt by recrystallization may include: preparing a sodium dodecyl sulfate solution; and adding $FeCl_3$ to the sodium dodecyl sulfate solution. Furthermore, the method may further include: dissolving, in methanol, a precipitate generated in the sodium dodecyl sulfate solution by the addition of $FeCl_3$ to prepare a methanol solution; and adding deionized water to the methanol solution to precipitate recrystallized $Fe(DS)_3$.

A PEDOT film according to another embodiment of the present disclosure may be a PEDOT film having a lamella structure in which at least one anionic molecule is doped between layers of PEDOT molecules, wherein the anionic molecule may be a $CH_3(CH_2)_nSO_4^-$ (n=7-17) dopant anion having a hydrocarbon chain length of 8C to 18C. Here, two anionic molecules may be doped between the layers of the PEDOT molecules.

Advantageous Effects

According to the present disclosure, by doping the PEDOT film with dodecyl sulfate, there is an effect of providing a PEDOT film having excellent electrical conductivity so as to be capable of replacing a metal electrode.

In addition, according to the present disclosure, there is an effect of providing a PEDOT film excellent in mechanical durability, flexibility, visible light transmittance, and aqueous solution resistance.

In addition, according to the present disclosure, by using vapor phase polymerization using a dodecyl sulfate metal salt such as $Fe(DS)_3$ as an oxidizing agent, there is an effect of providing a method capable of forming a high-quality PEDOT film without requiring the use of an inhibitor.

In addition, according to the present disclosure, by using freeze drying when synthesizing $Fe(DS)_3$, there is an effect of providing a high-purity, high-quality $Fe(DS)_3$ oxidizing agent that can be used for vapor phase polymerization of a PEDOT film.

DESCRIPTION OF DRAWINGS

FIG. 8 illustrates an observation result of morphology of a PEDOT film formed according to an embodiment of the present disclosure.

FIG. 14 illustrates in-plane XRD and out-of-plane GIWAXS analysis results of a dodecyl sulfate-doped PEDOT thin film according to an embodiment of the present disclosure.

MODE FOR INVENTION

Figure 1:
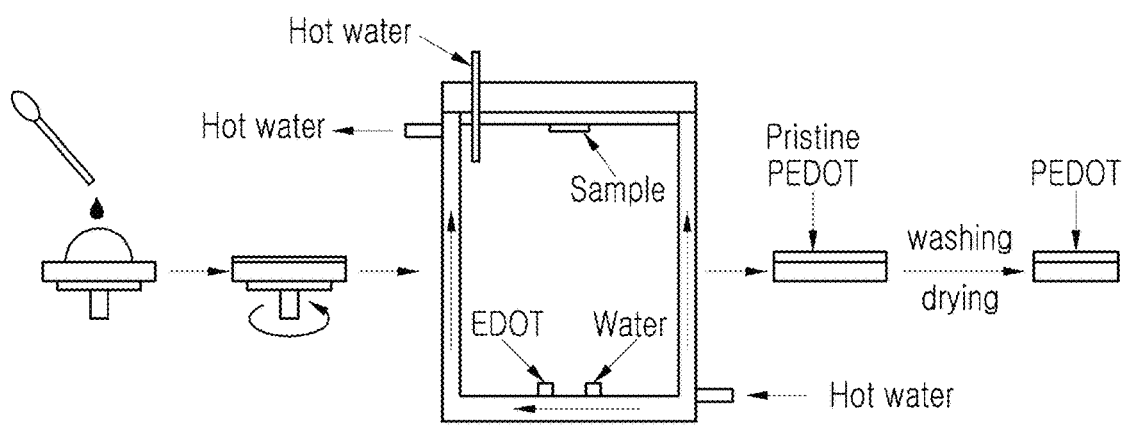
FIG. 1 is a view describing a method of forming a dodecyl sulfate-doped PEDOT film according to the present disclosure.

Hereinafter, the present disclosure will be described in detail with reference to the accompanying drawings. The following description includes specific embodiments, but the present disclosure is not limited or restricted by the described embodiments. In the following description, it is to be noted that, when the functions of conventional elements and the detailed description of elements related with the present disclosure may make the gist of the present disclosure unclear, a detailed description of those elements will be omitted.

The present inventors found that significantly high electrical conductivity is obtained when dodecyl sulfate was doped on a PEDOT film in the process of conducting a study to form a PEDOT film having an electrical conductivity high enough to replace a metal electrode, and thus the present disclosure was achieved. In particular, a dodecyl sulfate-doped PEDOT film according to the present disclosure is excellent in electrical conductivity as well as mechanical durability, visible light transmittance, and aqueous solution resistance, and thus can find successful application in various flexible devices such as flexible displays and bio devices.

In addition, the present disclosure discloses a method of manufacturing a PEDOT film having such excellent properties. The method of manufacturing the PEDOT film according to the present disclosure includes a method of forming a film by vapor phase polymerization using a dodecyl sulfate metal salt as an oxidizing agent, and a method of preparing a high-quality dodecyl sulfate metal salt oxidizing agent.

Formula 1 below is a formula of PEDOT and dodecyl sulfate dopant constituting the dodecyl sulfate-doped PEDOT film according to the present disclosure.

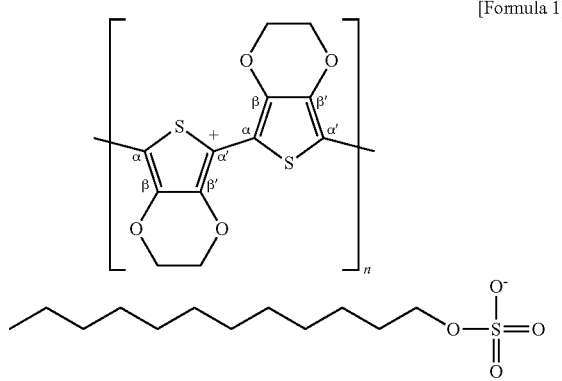

[Formula 1]

The amount of dodecyl sulfate in the dodecyl sulfate-doped PEDOT film according to the present disclosure may be in the range of 5 to 50 wt %, preferably in the range of 20 to 45 wt %, and more preferably in the range of 30 to 40 wt %.

The dodecyl sulfate-doped PEDOT film according to the present disclosure has excellent electrical conductivity so as to be capable of being used as an electrode of an electronic device, and the electrical conductivity may be equal to or greater than 5,500 S/cm, preferably equal to or greater than 9,000 S/cm, and more preferably equal to or greater than 10,000 S/cm.

The dodecyl sulfate-doped PEDOT film according to the present disclosure has excellent light transmittance so as to be capable of being used in a display, and may have a light transmittance of equal to or greater than 90% at a thickness of about 20 nm for a wavelength of 550 nm.

The dodecyl sulfate-doped PEDOT film according to the present disclosure has excellent mechanical properties so as to be capable of being used in a flexible electronic device. For example, the change in electrical resistance may be equal to or less than 9% even after performing a bending cycle of 300,000 times. In addition, the increase in electrical resistance may be equal to or less than 10% even after stretching the PEDOT film in length by about 30% by pulling the film in opposite directions.

In addition, the dodecyl sulfate-doped PEDOT film according to the present disclosure may have excellent water-resistant properties so as to be capable of being used in a bio device. For example, when measuring sheet resistance while the film is immersed in deionized (DI) water for a long period of time, the increase in electrical resistance may be equal to or less than 5% even after immersion for 20 days.

Figure 2:
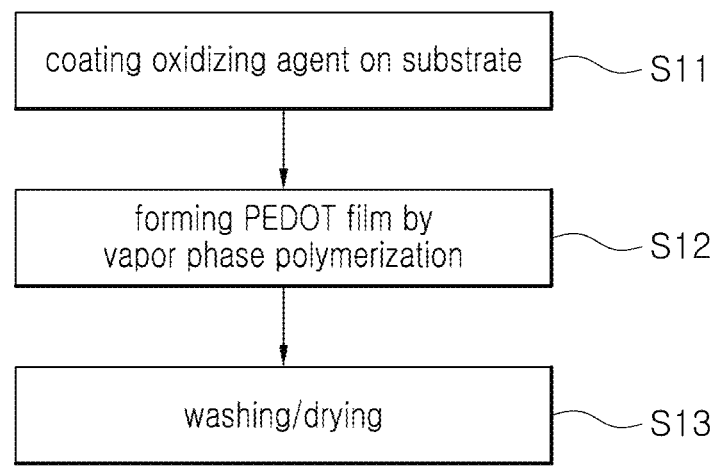
FIG. 2 is a flow chart of the method of forming the dodecyl sulfate-doped PEDOT film according to the present disclosure.

FIG. 1 and FIG. 2 are a view and a flow chart respectively describing a method of forming a dodecyl sulfate-doped PEDOT film according to the present disclosure.

Referring to FIGS. 1 and 2, the method of forming the dodecyl sulfate-doped PEDOT film according to the present disclosure includes coating an oxidizing film on a substrate (S11), forming a PEDOT film by vapor phase polymerization (S12), and performing washing and drying (S13).

First, the coating of the oxidizing film on the substrate (S11) is a step of coating an oxidizing agent acting as a catalyst for forming the PEDOT film on the substrate. The coating of the oxidizing agent may be performed by a spin coating method in which a solution including an oxidizing agent is discharged onto a surface of a substrate supported on a spin head, and the spin head is rotated at high speed to form a uniform oxidizing film.

As the oxidizing agent, a dodecyl sulfate metal salt having a formula of $M_x(DS)_y$ may be used. Here, DS is dodecyl sulfate, and M is a metal and may be Fe, Cr, Co, Ni, Mn, V, Rh, Au, Cu, or Mo, but is not limited thereto. For example, $Fe(DS)_3$ may be used as the oxidizing agent. In the present disclosure, by forming the PEDOT film by vapor phase polymerization in which the dodecyl sulfate metal salt is used as the oxidizing agent, the dodecyl sulfate-doped PEDOT film can be formed. In addition, by using the dodecyl sulfate metal salt as the oxidizing agent, a high-quality PEDOT film with few defects can be formed without the use of an inhibitor.

Next, in step S12, the substrate coated with the oxidizing agent film is mounted in a vapor phase polymerization chamber. At this time, as illustrated in FIG. 1, the substrate may be mounted on the top of the chamber so that the oxidizing agent film is oriented downward. Containers respectively including EDOT monomers and water are disposed on the bottom of the chamber, and the vaporized EDOT monomers and water reach the substrate. By the vapor phase polymerization having such a construction, the PEDOT film is formed on the substrate. At this time, the temperature inside the chamber may be controlled by circulating temperature-controlled hot water through a flow path formed in a chamber wall, and a temperature sensor for measuring temperature may be installed inside the chamber. Although FIG. 1 illustrates the substrate is mounted on the top of the chamber, the substrate may be mounted on the bottom of the chamber.

The substrate on which the PEDOT film is formed is unloaded in the vapor phase polymerization chamber, followed by washing and drying (S13). The washing may be to remove excess oxidizing agent and EDOT monomers remaining on a film surface, and may be performed using ethanol. After the washing, the drying may be performed at a temperature of about 70° C. for 1 to 2 hours to remove a washing solution.

Figure 3:
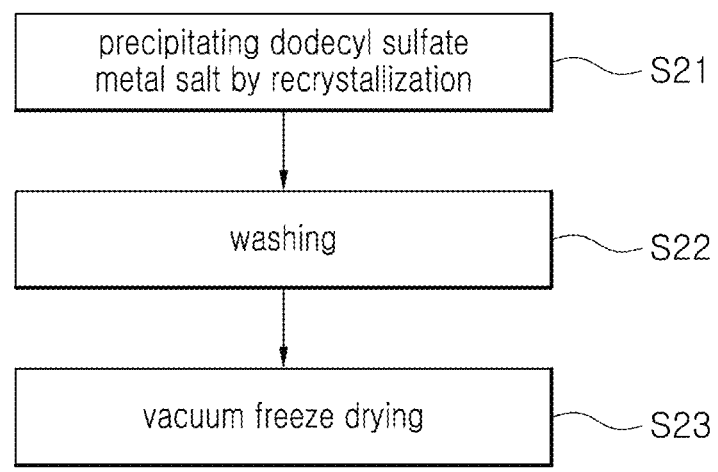
FIG. 3 is a flow chart of a method of preparing a dodecyl sulfate metal salt oxidizing agent according to the present disclosure.

FIG. 3 is a flow chart of a method of preparing a dodecyl sulfate metal salt oxidizing agent according to the present disclosure.

Referring to FIG. 3, first, a dodecyl sulfate metal salt is precipitated by recrystallization (S21). Here, recrystallization may be a method of precipitating the dodecyl sulfate metal salt by adding a metal compound (e.g., metal chloride) to a solution in which dodecyl sulfate is dissolved. At this time, the metal compound may be added in the form of an aqueous solution to the solution in which dodecyl sulfate is dissolved, and may be added while stirring the solution so as to be uniformly mixed.

Step S21 may further include removing impurities by centrifugation. For example, a precipitate obtained by adding a metal compound to a dodecyl sulfate solution may include impurities, and the precipitate may be dissolved in methanol or the like, followed by centrifugation to remove undissolved impurities. A final dodecyl sulfate metal salt precipitate may be obtained from the solution from which the impurities have been removed.

Next, the precipitated dodecyl sulfate metal salt is subjected to washing (S22) and then vacuum freeze drying (S23). The washing may be performed repeatedly using DI water, and the vacuum freeze drying may be performed under a reduced pressure atmosphere.

Figure 4:
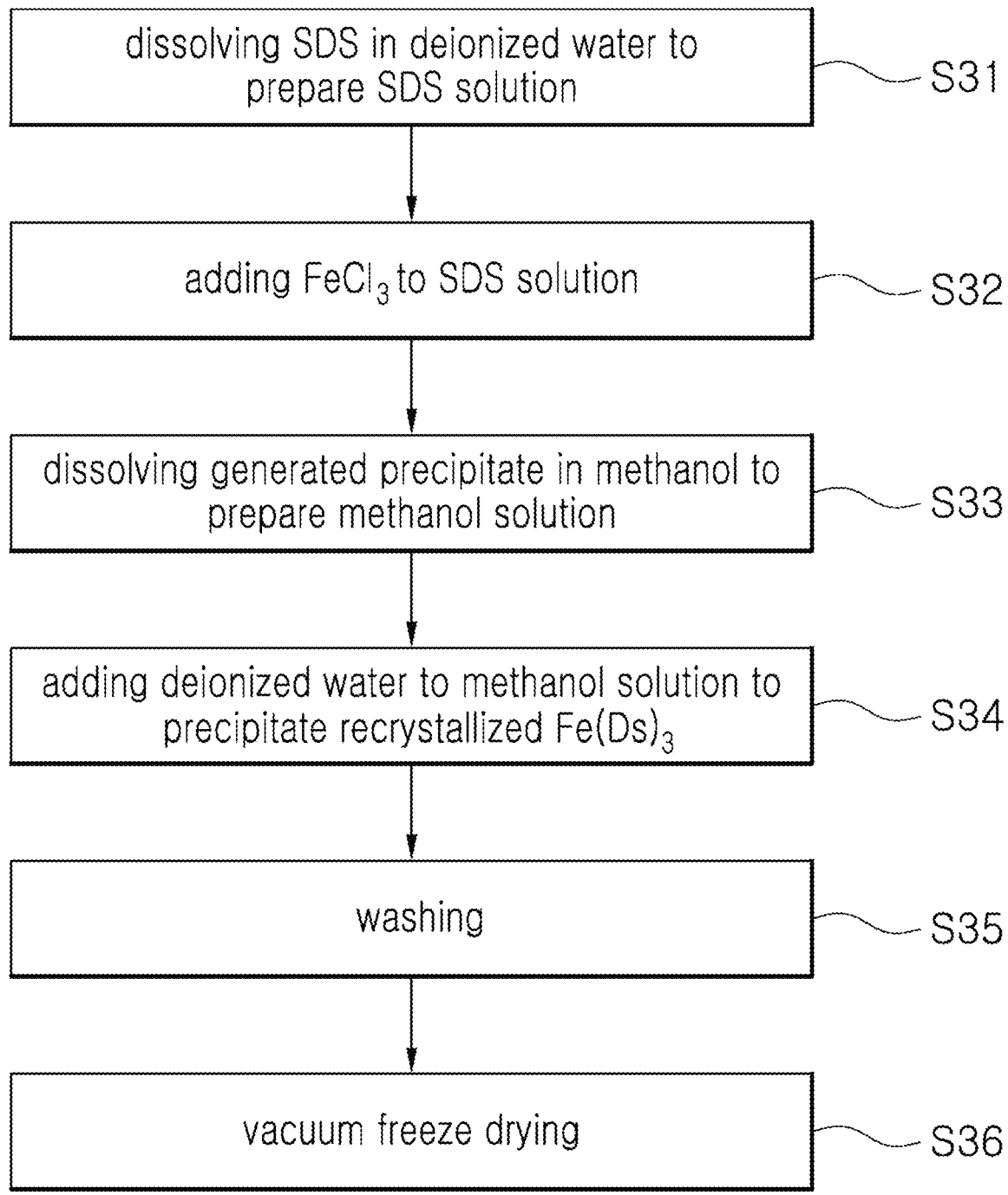
FIG. 4 is a flow chart of a method of preparing a $Fe(Ds)_3$ oxidizing agent according to an embodiment of the present disclosure.

FIG. 4 is a flow chart illustrating in detail a method of preparing a $Fe(DS)_3$ oxidizing agent according to an embodiment of the present disclosure.

Referring to FIG. 4, first, sodium dodecyl sulfate (SDS) is dissolved in DI water to prepare an SDS solution (S31). At this time, SDS may be dissolved while stirring until a transparent SDS solution is obtained.

Next, $FeCl_3$ is added to the SDS solution (S32). $FeCl_3$ may be added to the SDS solution in the form of an aqueous solution.

Next, a precipitate generated in the SDS solution by the addition of $FeCl_3$ is dissolved in methanol to prepare a methanol solution (S33). The precipitate may be repeatedly washed with DI water and then dissolved in methanol, and the methanol solution may be subjected to centrifugation at high speed to remove undissolved impurities.

DI water is added to the methanol solution from which impurities have been removed to precipitate recrystallized $Fe(DS)_3$ (S34). The precipitated $Fe(DS)_3$ is repeatedly washed, followed by drying by vacuum freeze drying, and the drying is preferably performed for at least 2 days.

Hereinafter, the present disclosure will be described in more detail on the basis of specific examples.

1. Experimental Method
(1) Preparation of $Fe(DS)_3$ Oxidizing Agent 10.2520 g of sodium dodecyl sulfate (SDS) was dissolved in DI water at 40° C., and stirred until it became transparent to obtain a 0.148 mol/L SDS solution. While stirring the SDS solution, a 0.197 mol/L $FeCl_3$ aqueous solution was slowly added so that the molar ratio between SDS and $FeCl_3$ was 3:1. A generated precipitate was repeatedly washed at least 10 times with DI water, dissolved in 45 ml methanol, followed by centrifugation at 5000 rpm to remove undissolved impurities. 200 ml of DI water was added while slowly stirring the methanol solution from which impurities were removed. $Fe(DS)_3$ precipitated by recrystallization from the solution was repeatedly washed at least 5 times, and then dried by vacuum freeze drying for at least 2 days.

(2) Formation of PEDOT Film

Various substrates, such as a silicon substrate and a PET substrate on which a thermal oxide film was formed, were ultrasonically cleaned for 30 minutes in ethanol, and then a solution including 10 wt % to 60 wt % of an oxidizing agent was coated on the substrate by spin coating to form an oxidizing agent film on the substrate.

The substrate coated with the oxidizing agent film was mounted in a vapor phase polymerization chamber so that the oxidizing agent film faced downward, and then EDOT monomers and water provided in the chamber were vaporized to form a PEDOT film on the substrate. At this time, a chamber temperature was adjusted to 50° C. by circulating hot water on a chamber wall, and the chamber temperature was monitored with a temperature sensor provided inside the chamber. The film was washed with ethanol to remove excess oxidizing agent and EDOT monomers, and then dried at 70° C. for 1 hour under reduced pressure to remove ethanol.

(3) Analysis of Characteristics

Thermal stability of $Fe(DS)_3$ was analyzed by differential scanning calorimeter (DSC) and thermogravimetric analysis (TGA).

Morphology of the PEDOT film was analyzed using a field emission scanning electron microscope (FE-SEM) and an atomic force microscope (AFM). After measuring sheet resistance R of a PEDOT film using a four-point probe, electrical conductivity thereof was calculated using a film thickness measured by the FE-SEM.

In addition, PEDOT film analysis was performed using X-ray photoelectron spectroscopy (XPS), Raman spectroscopy, grazing incidence X-ray diffraction, etc.

2. Result of Analysis of Characteristics of $Fe(DS)_3$ Oxidizing Agent

Table 1 illustrates an XPS analysis result of a prepared $Fe(DS)_3$ oxidizing agent. Cl (2p) was found to have a concentration of 0%, and it was confirmed that a high purity oxidizing agent from which Cl ions were completely removed was obtained by an oxidizing agent preparation method according to the present disclosure.

TABLE 1

| Ingredient | Amount (atomic %) |
|---|---|
| C (1 s) | 66.41 |
| Cl (2 p) | 0.00 |
| Fe (2 p) | 1.98 |
| S (2 p) | 8.17 |
| O (1 s) | 23.43 |

Figure 5:
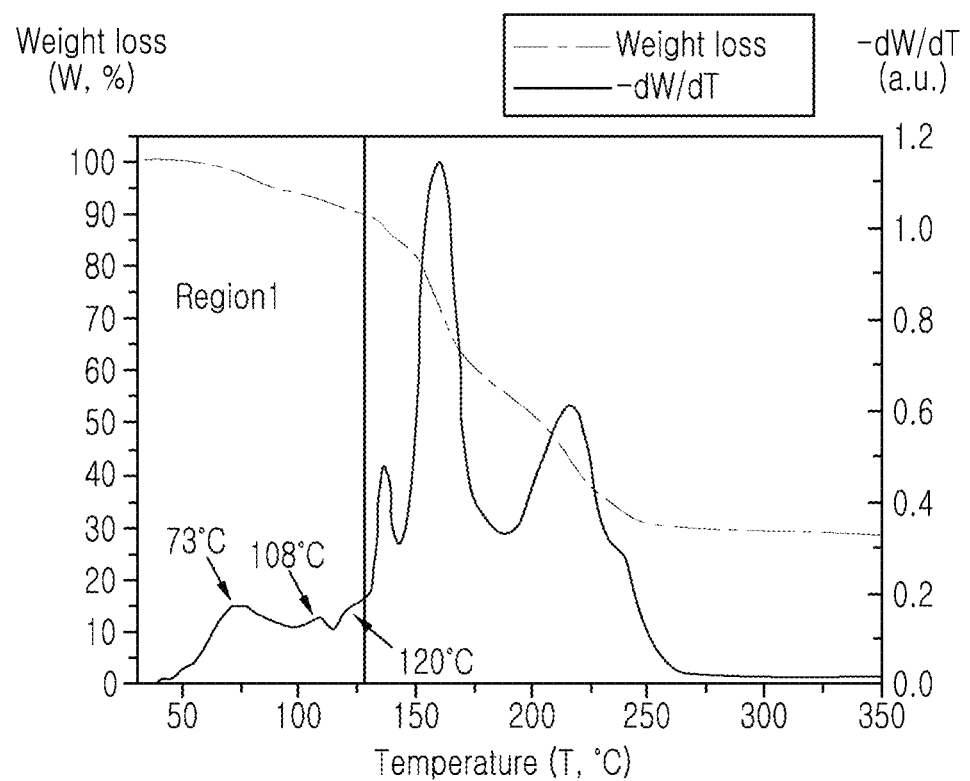
FIG. 5 illustrates a TGA analysis result of a $Fe(DS)_3$ oxidizing agent prepared according to an embodiment of the present disclosure.

FIG. 5 illustrates a TGA analysis result. As can be seen in a weight loss graph of FIG. 5, several different slopes are observed in the range of 30 to 350° C. Of these, a first weight loss that appears in a first region (Region 1) in the range of 30 to 126° C. is due to the release of water molecules included in an oxidizing agent. Based on a weight loss (10.2%) in the above-temperature range, the exact formula of the oxidizing agent prepared according to the embodiment of the present disclosure is calculated as $Fe(DS)_3 \cdot 5.3H_2O$.

Figure 6:
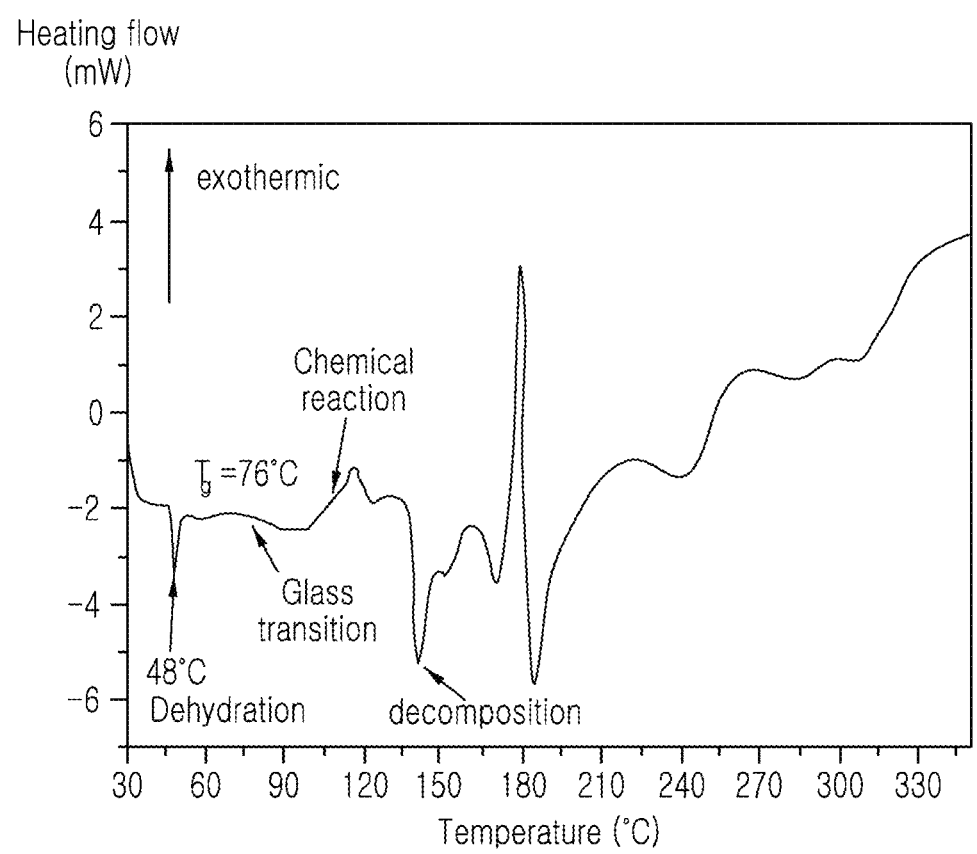
FIG. 6 illustrates a DSC analysis result of the $Fe(DS)_3$ oxidizing agent prepared according to the embodiment of the present disclosure.
Figure 7:
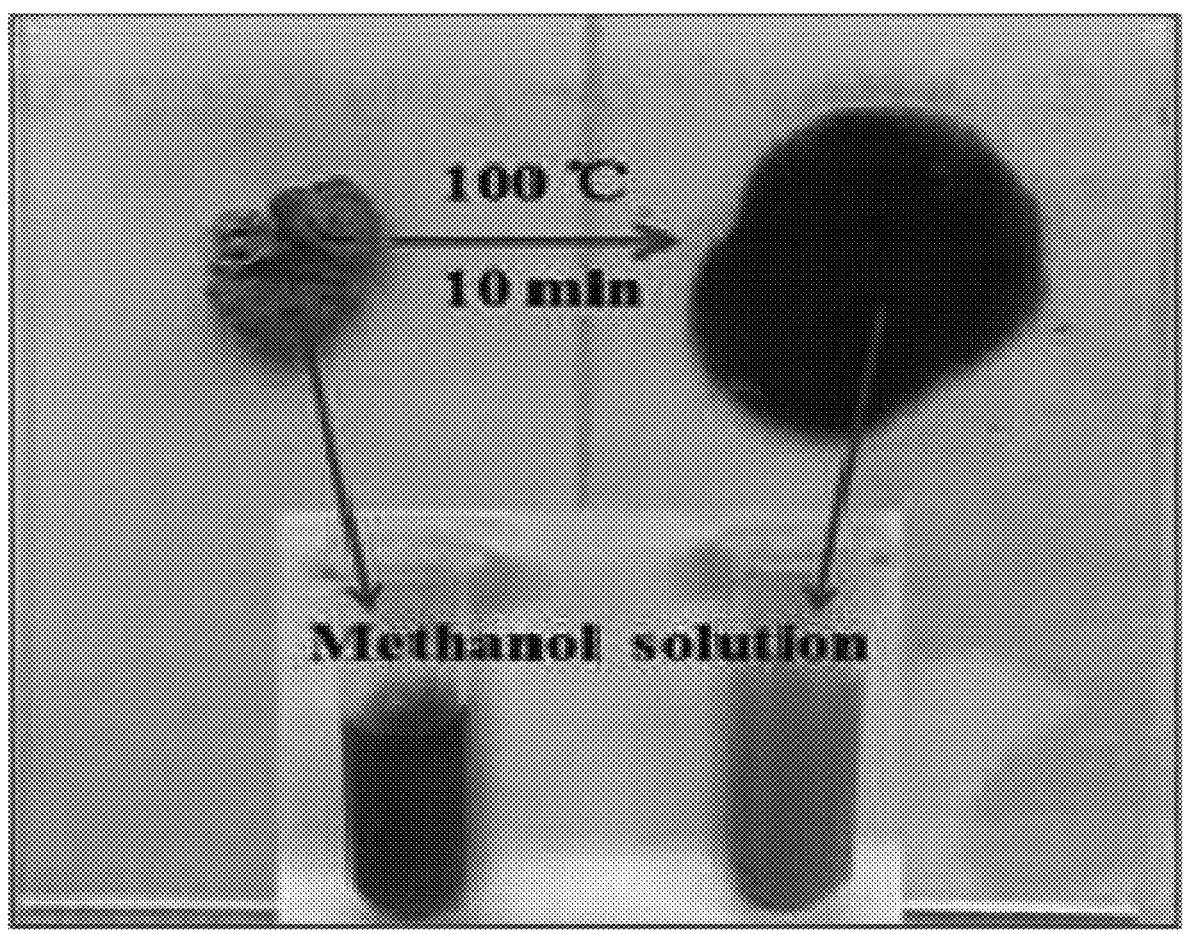
FIG. 7 illustrates a result of heat treatment performed at 100° C. on the $Fe(DS)_3$ oxidizing agent prepared according to the embodiment of the present disclosure.

FIG. 6 illustrates a DSC analysis result of the oxidizing agent prepared according to the embodiment of the present disclosure. It is confirmed that an endothermic peak related to the release of water molecules appears at about 48° C. It is believed that the peak at about 76° C. is due to the formation of a typical intermediate liquid crystalline phase, and an endothermic reaction that starts at about 97° C. and peaks at 116° C. is due to a chemical transformation of $Fe(DS)_3$. A result of observing the effect of this chemical transformation is illustrated in FIG. 7. It was observed that the $Fe(DS)_3$ oxidizing agent prepared according to the embodiment of the present disclosure changed from brown to black when subjected to heat treatment at 100° C. for 10 minutes, and the $Fe(DS)_3$ oxidizing agent was dissolved in methanol before heat treatment to become a transparent brown colored solution, whereas an opaque suspension was formed after heat treatment.

It is believed that a strong endothermic peak at 140° C. is due to chemical decomposition of compounds.

From this thermal analysis result, it can be seen that the Fe(DS)$_3$ oxidizing agent is in a chemically stable state at a temperature of about equal to or less than 76° C., which means that it is desirable to control the temperature of a preparation process of the Fe(DS)$_3$ oxidizing agent to not exceed about 76° C. This is also related to the fact that for drying of the Fe(DS)$_3$ oxidizing agent in the embodiment of the present disclosure, vacuum freeze drying was performed instead of a conventional high-temperature heat treatment. Through vacuum freeze drying, it was possible to prepare a high-quality Fe(DS)$_3$ oxidizing agent that can be used to form a PEDOT film by vapor phase polymerization.

3. Result of PEDOT Film Analysis (1) Result of Morphology Analysis

FIG. 8 illustrates a result of analyzing morphology of a PEDOT film formed by vapor phase polymerization using the Fe(DS)$_3$ oxidizing agent according to the embodiment of the present disclosure using an AFM and a FE-SEM. FIGS. 8(a) to 8(d), FIG. 8(e), and FIG. 8(f) illustrate a result of forming a PEDOT film on a PET substrate, a PI substrate, and a SiO$_2$ substrate, respectively.

According to an AFM analysis result illustrated in FIG. 8(a), surface roughness (root-mean-square (RMS) roughness) of the PEDOT film was about 1.87 nm, which means that a flat surface was obtained. In addition, according to FE-SEM images, it was confirmed that a smooth surface with high density was observed regardless of the substrate type, so that a uniform PEDOT film was grown on each substrate.

(2) Result of Analysis of Electrical and Optical Properties

Figure 9:
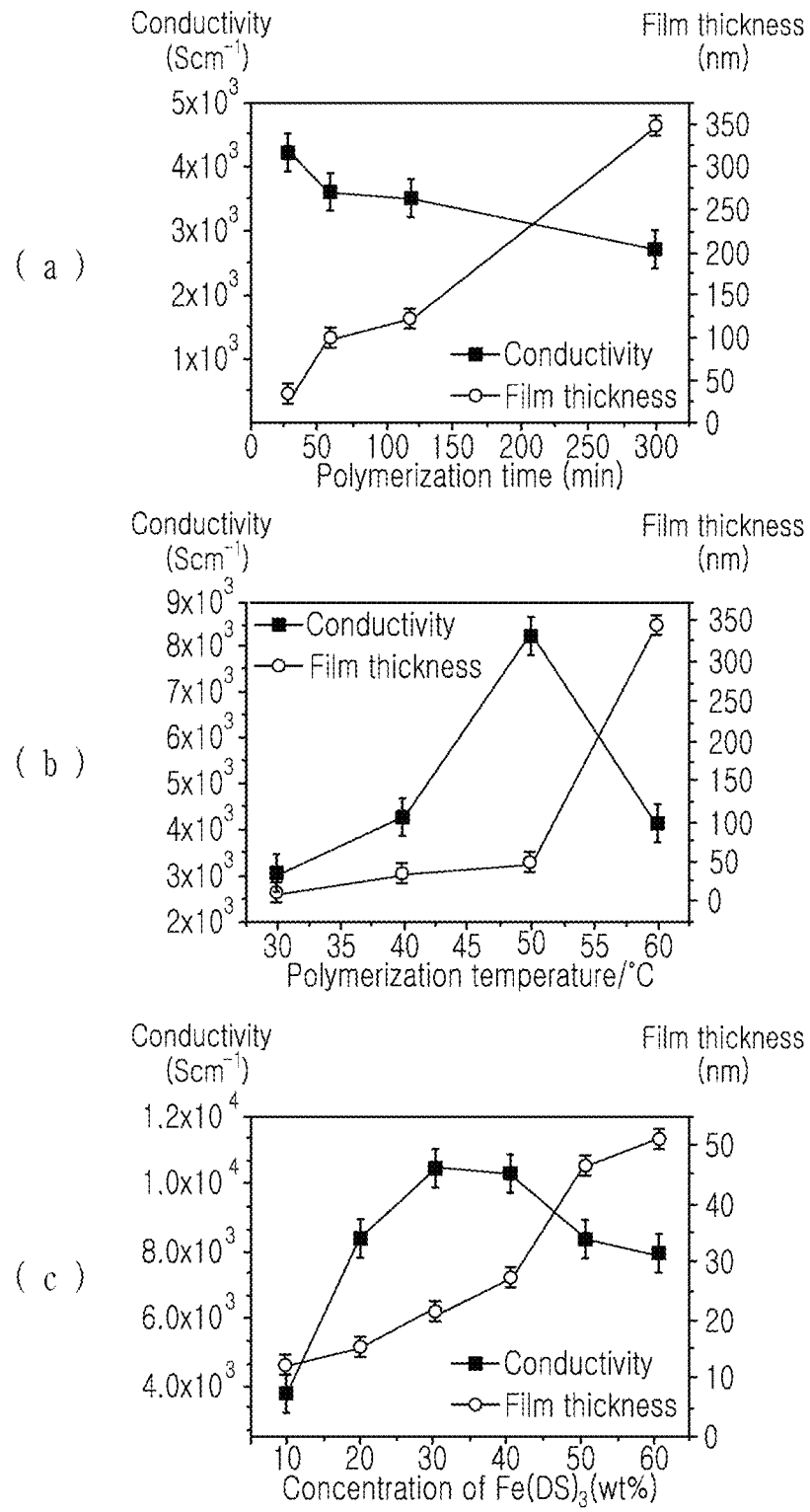
FIG. 9 illustrates a result of measuring electrical conductivity of the PEDOT film formed according to the embodiment of the present disclosure.

FIG. 9 illustrates a result of measuring electrical conductivity of a PEDOT film formed by vapor phase polymerization using the Fe(DS)$_3$ oxidizing agent according to the embodiment of the present disclosure. In FIG. 9, a result of using a PET substrate as a substrate is illustrated, but similar electrical conductivity characteristics were obtained regardless of the substrate type. FIGS. 9(a) to 9(c) illustrate changes in electrical conductivity according to polymerization time, polymerization temperature, and oxidizing agent concentration, respectively.

FIG. 9(a) illustrates a change in electrical conductivity according to polymerization time at a polymerization temperature of 40° C. and an oxidizing agent concentration of 50 wt %, and it was found that the electrical conductivity decreases despite the increase in film thickness as the polymerization time increases. Therefore, the polymerization time may be optimally selected as 30 minutes within the experimental range.

FIG. 9(b) illustrates a change in electrical conductivity according to the polymerization temperature at a polymerization time of 30 minutes and an oxidizing agent concentration of 50 wt %, and it was found that film thickness continuously increases as the polymerization temperature increases from 30° C. to 60° C., and in particular, a sharp increase appears at equal to or greater than 50° C., whereas a maximum electrical conductivity appears at 50° C. That is, the polymerization temperature may be selected as 50° C. within the experimental range.

FIG. 9(c) illustrates a result of an experiment of electrical conductivity according to an oxidizing agent concentration at an optimally selected polymerization time of 30 minutes and a polymerization temperature of 50° C. It was found that the electrical conductivity continuously increases as the oxidizing agent concentration increases from 10 wt % to 30 wt %, but begins to decrease again at the oxidizing agent concentration of equal to or greater than 30 wt %. Therefore, the oxidizing agent concentration may be optimally selected as 30 wt %, and the electrical conductivity at this time was 10,307±500 S/cm. Due to the fact that the highest electrical conductivity of a PEDOT film by vapor phase polymerization reported so far is 5,400 S/cm for a tosylate-doped PEDOT film, it can be found that the electrical conductivity of the PEDOT film formed according to the embodiment of the present disclosure is substantially double the electrical conductivity of the related art. In addition, electrical conductivity properties superior to those of the related art were obtained not only at the oxidizing agent concentration of 30 wt % but also in most oxidizing agent concentration ranges illustrated in FIG. 9(c). Therefore, it can be said that such high electrical conductivity properties of the PEDOT film according to the embodiment of the present disclosure is due to the effect of doping dodecyl sulfate using the Fe(DS)3 oxidizing agent.

Figure 10:
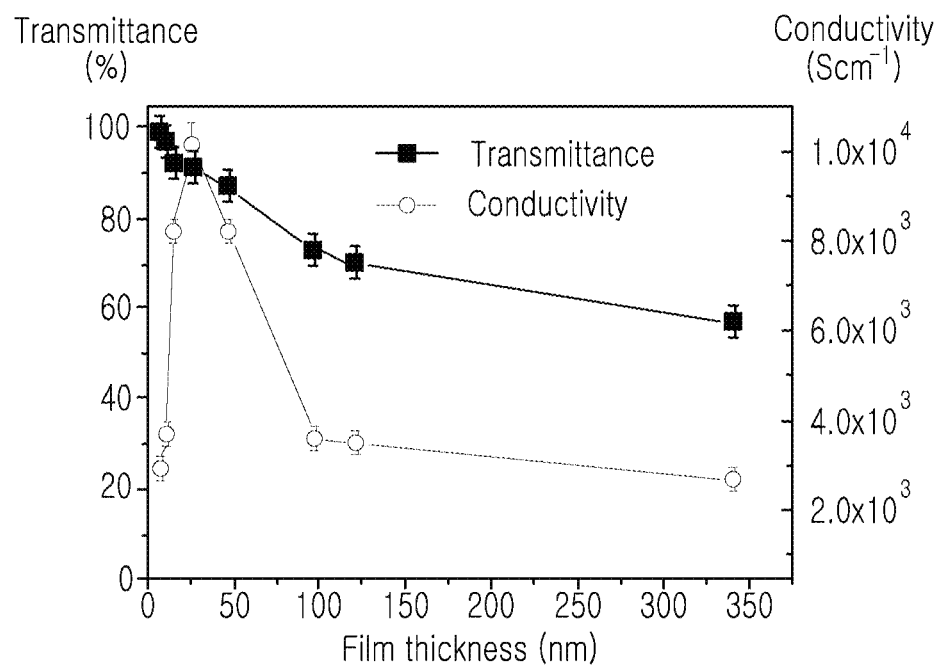
FIG. 10 is a graph of light transmittance at a wavelength of 550 nm according to thickness of a PEDOT film formed on a PET substrate.

FIG. 10 is a graph of light transmittance at a wavelength of 550 nm according to thickness of a PEDOT film formed on a PET substrate. It was found that the light transmittance was equal to or greater than 87% at a thickness of equal to or less than 47 nm, and the light transmittance was equal to or greater than 90% at a thickness of 21.3 nm. These light transmittances are at a level that can be sufficiently utilized as a transparent electrode of a display device, etc.

Table 2 illustrates the electrical and optical properties of the PEDOT film according to the substrate type. Regardless of the substrate type, the PEDOT film exhibited high electrical conductivity of about 10,000 S/cm and high light transmittance of equal to or greater than 90%.

TABLE 2

| Substrate | Thickness (nm) | Electrical Conductivity (Scm$^{-1}$) | Light Transmittance at 550 nm Wavelength (%) |
|---|---|---|---|
| PET | 21.3 | 10,110 ± 500 | 90.8 |
| PI | 22.8 | 9,856 ± 500 | 90.6 |
| SiO$_2$-wafer | 21.0 | 10,307 ± 500 | NA |

(3) Result of Doping Level Analysis

Figure 11:
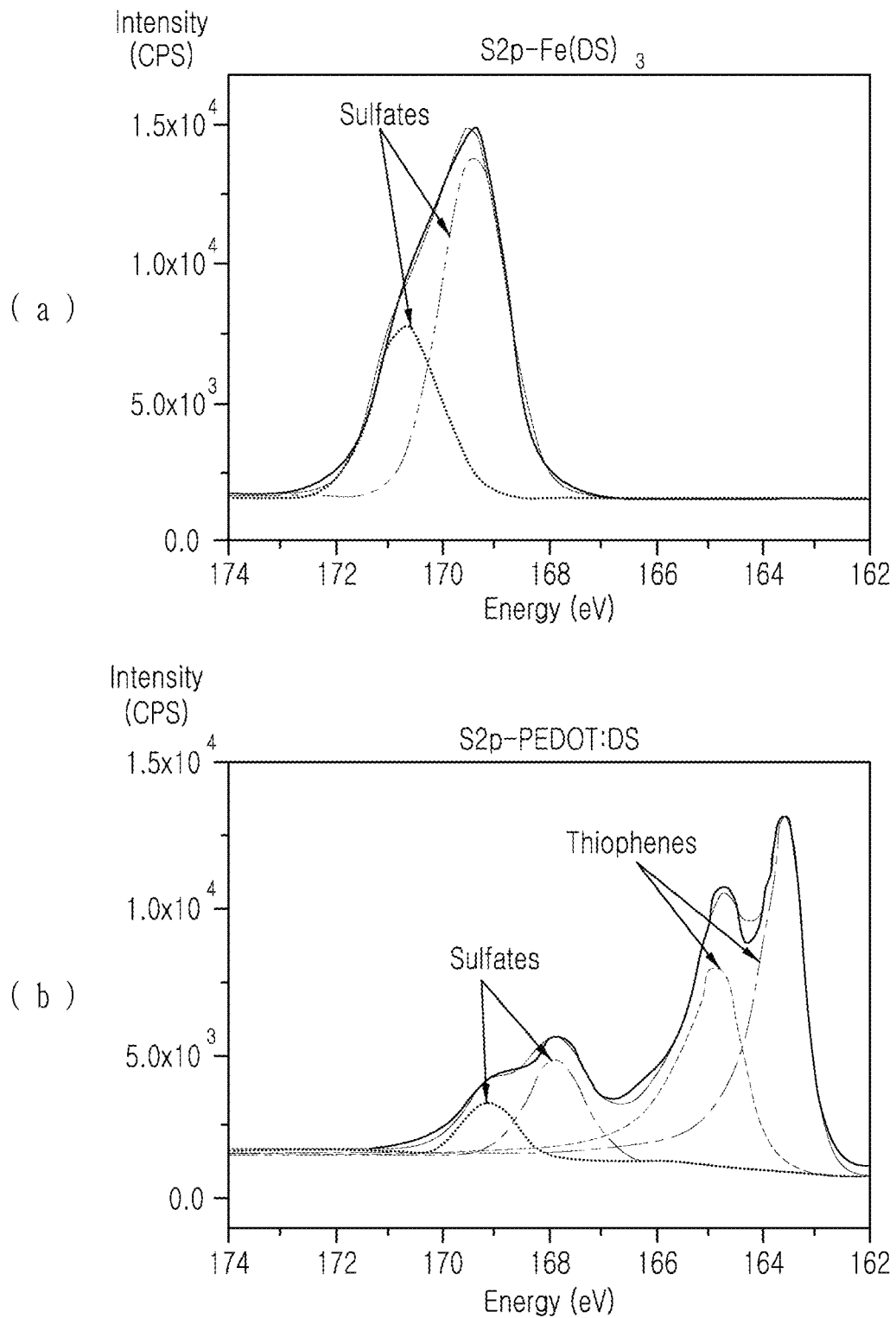
FIG. 11 illustrates an XPS analysis result of a $Fe(DS)_3$ oxidizing agent film (FIG. 11(a)) and a PEDOT film (FIG. 11(b)).

FIG. 11 illustrates an XPS analysis result of a Fe(DS)$_3$ oxidizing agent film (FIG. 11(a)) and a PEDOT film (FIG. 11(b)) formed thereon. Compared with the result illustrated in FIG. 11(a), two XPS bands appearing between 166 eV and 172 eV in FIG. 11(b) are S2p bands of a sulfur atom of a dodecyl sulfate (DS) component, and two XPS bands appearing between 162 eV and 166 eV in FIG. 11(b) are S2p bands of a sulfur atom in PEDOT. S2p peaks due to dodecyl sulfate (DS) appear at 167.65 eV and 169.13 eV in PEDOT, which is different from 169.5 eV and 170.5 eV in Fe(DS)$_3$. The doping level of dodecyl sulfate (DS) calculated from the ratio of XPS peaks in FIG. 11(b) was about 37%.

(4) Result of Analysis of Mechanical Properties

Figure 12:
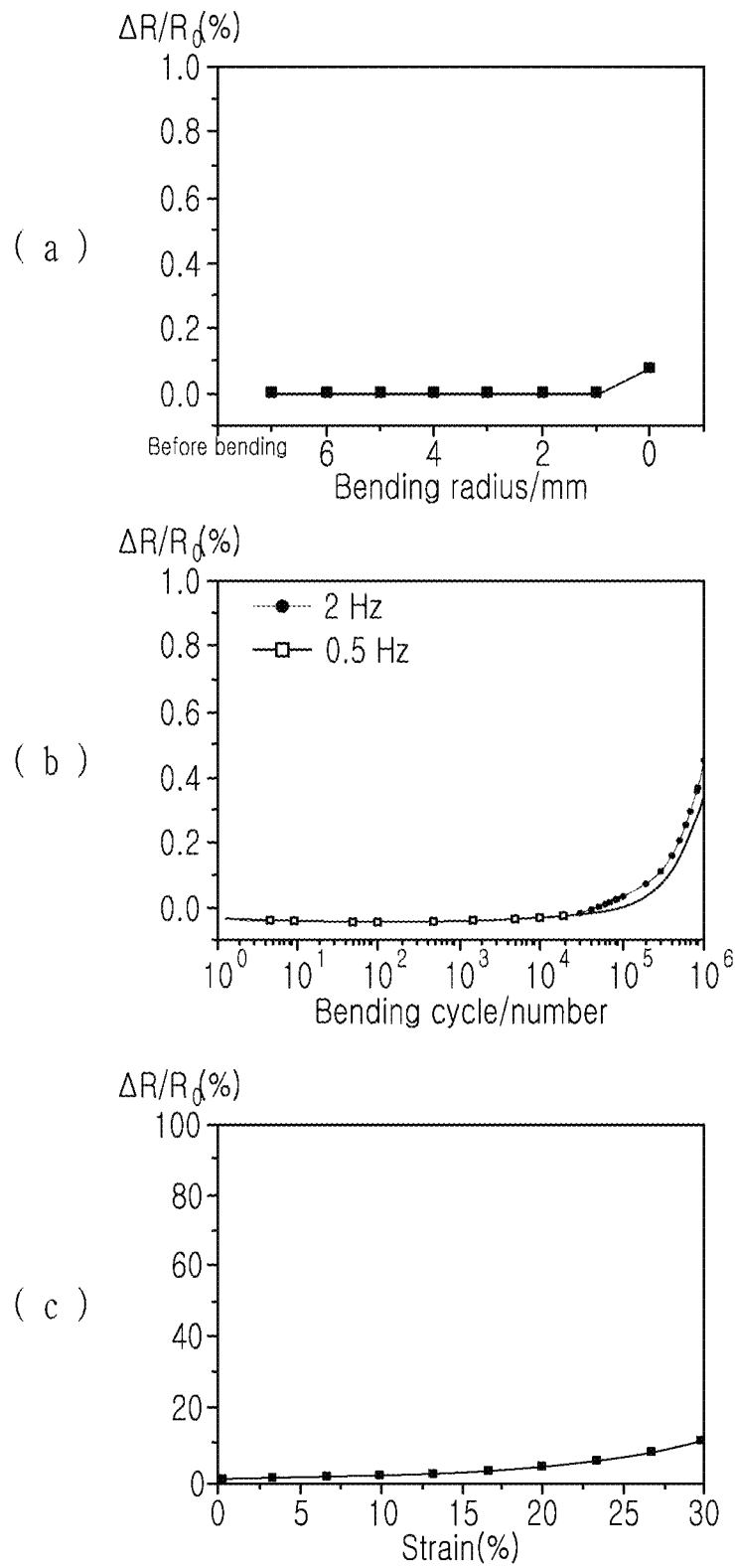
FIG. 12 illustrates a result of measuring mechanical properties of the PEDOT film according to the embodiment of the present disclosure.

FIG. 12(a) illustrates a result of measuring a change in electrical resistance after bending a PEDOT film sample formed on a PET substrate. It can be seen that there is little change in electrical resistance even until bending radius of curvature reaches 0 mm.

FIG. 12(b) illustrates a result of measuring a change in electrical resistance while repeating a bending cycle, and bending frequencies were 0.5 Hz and 2 Hz. It was confirmed that there is little change in electrical resistance even after 10,000 bending cycles regardless of frequency. In addition, it was also confirmed that the change in electrical resistance is only 7 to 10% even after performing 200,000 bending cycles, and specifically, the change in electrical resistance is equal to or less than 9% even after performing 300,000 bending cycles.

FIG. 12(c) illustrates a result of performing a stretch test after forming a PEDOT film on a polyurethane substrate. According to the result illustrated in FIG. 12(c), even when the PEDOT film was stretched in length by about 30% by pulling the film in opposite directions, the increase in electrical resistance was only at the level of 10%.

As such, it can be seen that the PEDOT film according to the embodiment of the present disclosure has a slight change in electrical resistance even by bending or stretching, and thus can be used in various flexible devices such as wearable electronic devices, flexible displays, and foldable batteries.

(5) Stability in Aqueous Solution

Figure 13:
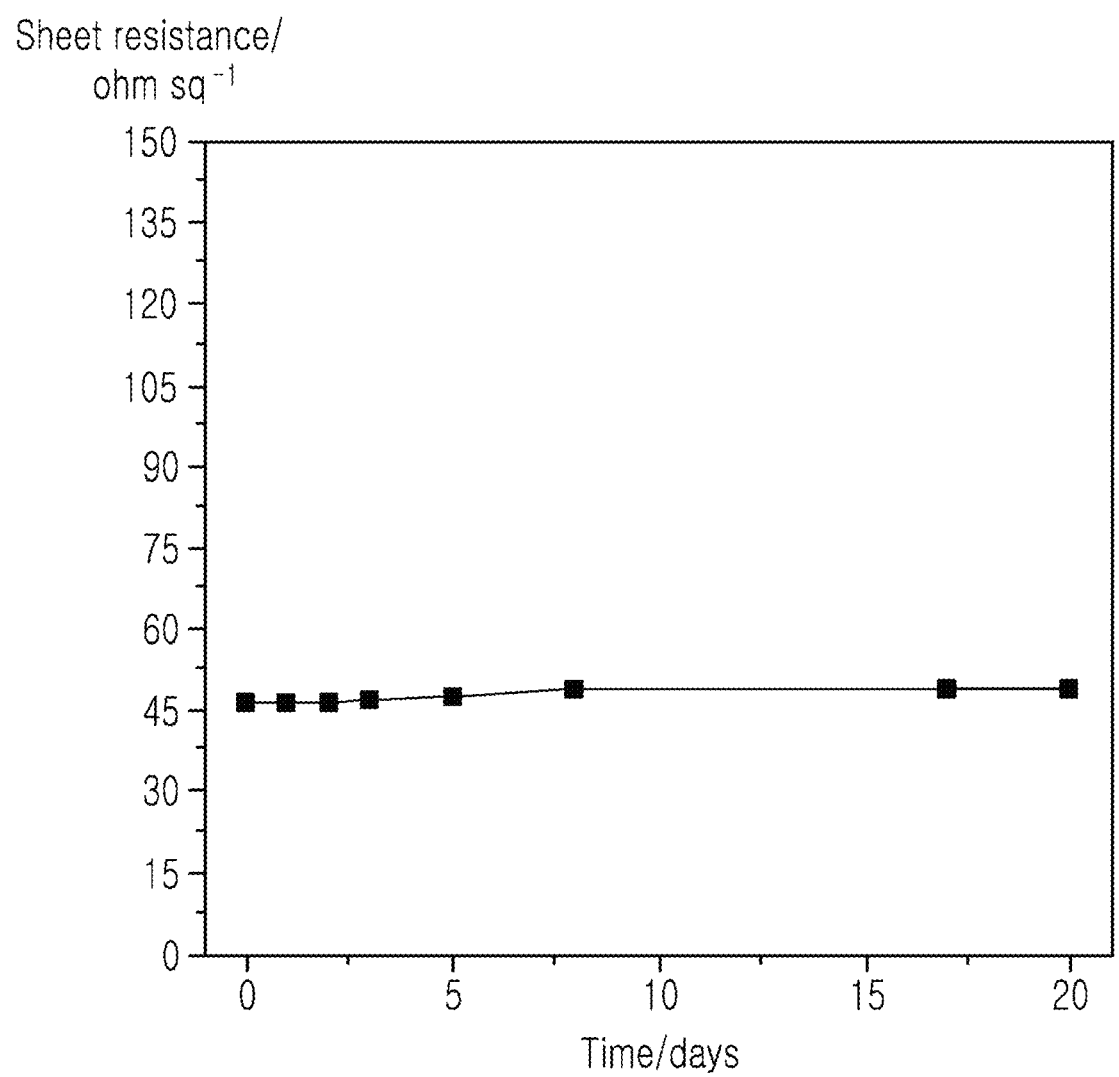
FIG. 13 illustrates a result of measuring a change in sheet resistance over time by immersing the PEDOT film according to the embodiment of the present disclosure in deionized water.

The PEDOT film according to the embodiment of the present disclosure was immersed in DI water to measure a change in sheet resistance over time to analyze water-resistant properties, and the result is illustrated in FIG. 13. The sheet resistance was maintained at equal to or less than 50 ohm/sq. even after immersion in DI water for 20 days at an initial sheet resistance of 46.1 ohm/sq., and it was confirmed that water resistance of the PEDOT film according to the embodiment of the present disclosure is very excellent.

(6) Crystal Structure Analysis

In-plane X-ray diffraction (XRD) and out-of-plane grazing incidence wide angle x-ray scattering (GIWAXS) analysis was carried out to analyze the crystal structure of a dodecyl sulfate-doped PEDOT thin film according to an embodiment of the present disclosure, and the results are illustrated in FIGS. 14(a) and 14(b), respectively.

The in-plane XRD result illustrated in FIG. 14(a) illustrates crystallinity on an x-y plane parallel to a surface of the PEDOT film, and a peak at $2\Theta=26.72°$ means that a $\pi$-$\pi$ stacking distance between PEDOT main chains is 0.34 nm. In addition, peaks at $2\Theta=19.792°$ and $36.256°$ are peaks in the 010 and 020 directions having periodicities of 0.45 nm and 0.49 nm, respectively, which means that an average packing distance of dodecyl sulfate anionic dopant molecules in the x-y direction is about 0.47 nm.

The out-of-plane GIWAXS result illustrated in FIG. 14(b) illustrates crystallinity in the z-axis direction, which is the thickness direction of the PEDOT film, and a peak at $2\Theta=6.7°$ means that a lamellar interlayer distance of PEDOT crystal along the (100) plane direction is 1.32 nm.

Figure 15:
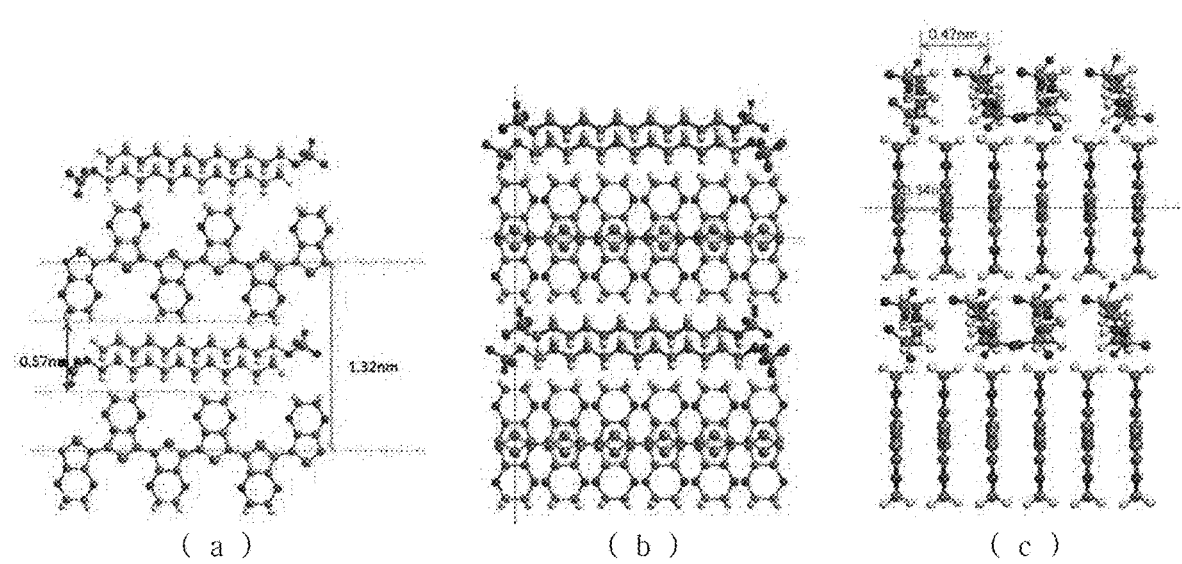
FIG. 15 illustrates a crystal structure of the dodecyl sulfate-doped PEDOT thin film according to the embodiment of the present disclosure.

According to structure prediction based on the above result of crystal structure analysis, the structure of the dodecyl sulfate-doped PEDOT film according to the embodiment of the present disclosure is as illustrated in FIG. 15.

In the x-y plane parallel to the surface of the PEDOT film, when the direction in which the PEDOT main chains are lined up is referred to as the x-axis direction, the direction perpendicular thereto is referred to as the y-axis direction, and the thickness direction of the PEDOT film is referred to as the z-axis direction, FIG. 15(a) is a cross-sectional view of the film as viewed in the x-axis direction, FIG. 15(b) is a perspective view of the film as viewed in the x-axis direction, and FIG. 15(c) is a perspective view of the film as viewed in the y-axis direction. FIG. 15 illustrates a structure inside one grain in the film. FIG. 15(a) illustrates that PEDOT molecules have a lamella structure, and the lamellar interlayer distance (the distance between PEDOT main chains) is 1.32 nm. This is supported by the out-of-plane GIWAXS result illustrated in FIG. 14(b). Here, considering the width of the PEDOT molecules, an effective space between layers of the PEDOT molecules is calculated to be 0.57 nm, which almost corresponds to a theoretical width of 0.56 nm in which two dodecyl sulfate molecules are stacked. That is, the PEDOT film according to the embodiment of the present disclosure may have a lamella structure in which the two dodecyl sulfate molecules are doped between the layers of the PEDOT molecules.

In the case of the structure in which the two dodecyl sulfate molecules are doped, hydrophobic ethylene (—CH2CH2-) groups periodically exposed above and below a PEDOT lamella layer exhibit very close Van der Waals interactions with a dodecyl group of a dopant molecule, which is advantageous in terms of energy.

FIG. 15(b) is a perspective view of the film as viewed in the x-axis direction, and FIG. 15(a) illustrates only one layer in the x-axis direction, whereas FIG. 15(b) illustrates two layers overlapped in the x-axis direction. Referring to FIG. 15(b), two main chains of PEDOT form two lamella layers, and each of the lamella layers includes a total of 12 EDOTs. That is, a total of 24 EDOT molecules exist in FIG. 15(b), and 8 dodecyl sulfate molecules are disposed between the lamella layers. This is in good agreement with the dodecyl sulfate doping level of about 37% calculated from the XPS analysis.

FIG. 15(c) is a perspective view of the film as viewed in the y-axis direction, illustrating a crystal structure in which a total of six PEDOT main chains are stacked by $\pi$-$\pi$ stacking to form two lamella layers above and below. Here, the $\pi$-$\pi$ stacking distance between the PEDOT main chains is 0.34 nm, and the distance between hydrocarbon chains of dodecyl sulfate dopant molecules is 0.47 nm. This is supported by the in-plane XRD result illustrated in FIG. 14(a).

According to such a crystal structure, it can be seen that dodecyl sulfate located above and below a PEDOT crystal layer is doped very efficiently, and at the same time long hydrocarbon chains densely surround the crystal layer. This structure realizes high electrical conductivity, significantly high elasticity, and excellent mechanical durability of the dodecyl sulfate-doped PEDOT film according to the embodiment of the present disclosure. In addition, according to the crystal structure in which highly hydrophobic hydrocarbon chains densely surround each PEDOT crystal layer, it is expected that significantly high film quality and electrical conductivity can be maintained in an aqueous solution or even at high humidity. This is in good agreement with the result of excellent aqueous solution stability of the dodecyl sulfate-doped PEDOT film.

In the embodiment of the present disclosure, it has been described that the dopant anion is limited to dodecyl sulfate. However, according to the crystal structure illustrated in FIG. 15, it can be expected that the dopant anion may have a hydrocarbon chain length slightly shorter or slightly longer than that of dodecyl sulfate. According to an experiment conducted by the present inventors, as a result of applying dopant anions having a hydrocarbon chain length in the range of 8C to 18C, more excellent properties than those of PEDOT films reported in the related art could be obtained although the levels of excellent were not the same. That is, it should be understood that a PEDOT film doped with a dopant anion of $CH_3(CH_2)_nSO_4$ (n=7-17) is also included within the scope of the present disclosure.

Hereinabove, the present disclosure is described with reference to the limited embodiments and drawings. However, the description proposed herein is just a preferable example for the purpose of illustrations only, not intended to limit the scope of the present disclosure, so it will be understood by those skilled in the art that the present disclosure can be modified in various forms without departing from the technical spirit of the present disclosure.

Therefore, the scope of the present disclosure should be determined on the basis of the descriptions in the appended claims, and all equivalents thereof should belong to the scope of the present disclosure.

The invention claimed is:

1. A PEDOT film including dodecyl sulfate as a dopant, wherein the PEDOT film is formed by vapor phase polymerization using a dodecyl sulfate metal salt as an oxidizing agent, and
wherein the PEDOT film has an electrical conductivity of equal to or greater than 10,307 S/cm.

2. The PEDOT film of claim 1,
wherein the dodecyl sulfate metal salt is $Fe(DS)_3$.

3. The PEDOT film of claim 1,
wherein an amount of the dodecyl sulfate dopant is within a range of 5% to 50% by weight.

4. The PEDOT film of claim 1,
wherein the PEDOT film has a light transmittance of equal to or greater than 90% at a thickness of 20 nm for a wavelength of 550 nm.

5. The PEDOT film of claim 1,
wherein the PEDOT film has a change in electrical resistance equal to or less than 9% after 300,000 bending cycles, or a change in electrical resistance of equal to or less than 10% after stretching in length by 30%.

6. The PEDOT film of claim 1,
wherein the PEDOT film has a change in electrical resistance of equal to or less than 5% even after immersion in deionized water for at least 20 days.

7. The PEDOT film of claim 1,
wherein the PEDOT film has a lamella structure in which a dodecyl sulfate molecule is doped between layers of PEDOT molecules.

8. The PEDOT film of claim 7,
wherein two dodecyl sulfate molecules are doped between the layers of the PEDOT molecules.

9. An electronic device including:
the PEDOT film of claim 1.

10. The electronic device of claim 9,
wherein the PEDOT film is included as an electrode.

11. A method of manufacturing a PEDOT film, the method comprising:
coating, on a substrate, an oxidizing agent film including a dodecyl sulfate metal salt;
forming a PEDOT film on the substrate coated with the oxidizing agent film by vapor phase polymerization; and
washing and drying the PEDOT film wherein the PEDOT film includes dodecyl sulfate as a dopant and wherein the PEDOT film has an electrical conductivity of equal to or greater than 10,307 S/cm.

12. The method of claim 11,
wherein the dodecyl sulfate metal salt includes $Fe(DS)_3$.

13. The method of claim 11, wherein the method is free from use of an inhibitor.

* * * * *